(12) United States Patent
Srivastava et al.

(10) Patent No.: US 6,475,490 B1
(45) Date of Patent: Nov. 5, 2002

(54) COMPOSITIONS AND METHODS FOR PROMOTING TISSUE REPAIR USING HEAT SHOCK PROTEINS

(75) Inventors: Pramod K. Srivastava, Avon, CT (US); Rajiv Y. Chandawarkar, Akron, OH (US)

(73) Assignee: Fordham University, Bronx, NY (US)

( * ) Notice: Subject to any disclaimer, the term of this patent is extended or adjusted under 35 U.S.C. 154(b) by 0 days.

(21) Appl. No.: 09/174,884

(22) Filed: Oct. 19, 1998

(51) Int. Cl.[7] ............................................. A61K 39/385

(52) U.S. Cl. ................................ 424/193.1; 424/184.1; 424/194.1; 424/195.11; 424/85.1; 424/85.2; 424/85.4

(58) Field of Search ........................... 424/184.1, 193.1, 424/278.1, 194.1, 195.11, 85.1, 85.2, 85.4

(56) References Cited

U.S. PATENT DOCUMENTS

| | | | |
|---|---|---|---|
| 5,750,119 A | 5/1998 | Srivastava |
| 5,830,464 A | 11/1998 | Srivastava |
| 5,837,251 A | 11/1998 | Srivastava |
| 5,935,576 A | 8/1999 | Srivastava |

FOREIGN PATENT DOCUMENTS

| | | |
|---|---|---|
| WO | WO 95/15338 | 6/1995 |
| WO | WO 95/15339 | 6/1995 |

OTHER PUBLICATIONS

Moulin, V., 1995, "Growth factors in skin wound healing", European Journal of Cell Biology, 68:1–7.

Nath and Gulati, 1998, "Role of Cytokines in Healing Chronic Skin Wounds", Acta Haematol, 99:175–179.

Blachere et al., 1997, "Heat shock protein–peptide complexes, reconstituted in vitro, eleicit peptide specific cytotoxic T lymphocyte responses and tumor immunity", J. of Experimental Medicine 186(8):1315–1322.

Srivastava et al., 1994, "Heat shock protein–peptide complexes in cancer immunotherapy", Curr Opin Immunol. 6(5):728–32.

Haley and Berndt, "Handbook of Toxicology," Hemisphere Publishing Corporation (New York, 1987, pp. 128–134).

Haley and Berndt, "Handbook of Toxicology,"Hemisphere Publishing Corporation (New York, 1987, pp. 167–174).

Ortega et al., 1995, "Dietary nucleotides accelerate intestinal recovery after food deprivation in old rats," J. Nutr. 125:1413–18.

Raul et al., 1995, "Beneficial effects of L–arginine on intestinal epithelial restitution after ischemic damage in rats,", Digestion 56(5):400–5.

Ketteler et al., 1994, "Cytokines and L–arginine in renal injury and repair," Am J Physiol 267(2 Pt 2):F197–207.

Asea et al., 2000, "Hsp70 Stimulates Cytokine Production Through a CD14–dependant Pathway, Demonstrating its Dual Role as a Chaperone and Cytokine," Nature Medicine 6(4):435–438.

Singh–Jasuja et al., 2000, "The Heat Shock Protein Gp96 Induces Maturation of Dendritic Cells and Down–regulation of its Receptor," Eur. J. Immunol. 30:2211–2215.

Ankoma–Sey et al., 1998, "Coordinated induction of VEGF receptors in mesenchymal cell types during rat hepatic wound healing", Oncogene 17:115–121.

Barbul et al., 1995, "Immune involvement in wound healing", Otolaryngol Clin North Am 28:955–968.

Barbul et al., 1990, "Arginine enhances wound healing and lymphocyte immune responses in humans", Surgery 108:331–337.

Bennett and Schultz, 1993, "Growth factors and wound healing: biochemical properties of growth factors and their receptors", Am J Surg 165:728–737.

Bennett and Schultz, 1993, "Growth factors and wound healing: Part II. Role in normal and chronic wound healing", Am J Surg 166:74–81.

Boccacio and Steinman, 1996, "Multiple sclerosis: from a myelin point of view", J Neurosci Res 45:647–654.

Chesney et al., 1997, "The peripheral blood fibrocyte is a potent antigen–presenting cell capable of priming naive T cells in situ", Proc. Natl. Acad. Sci. USA 94:6307–6312.

Chesney and Bucala, 1997, "Peripheral blood fibrocytes: novel fibroblast–like cells that present antigen and mediate tissue repair", Biochem Soc Trans 25:520–524.

Compton et al., 1996, "The beneficial effect of enhanced macrophage function on the healing of bowel anastomoses", Am Surg 62:14–18.

Kartha and Toback, 1992, "Adenine nucleotides stimulate migration in wounded cultures of kidney epithelial cells", J Clin Invest 90:288–292.

Oberringer et al., 1995, "Differential expression of heat shock protein 70 in well healing and chronic human wound tissue", Biochem Biophys Res Comm 24:1009–1014.

Oemar and Luscher, 1997, "Connective tissue growth factor. Friend or foe?", Arterioscler Thromb Vasc Biol 17:1483–1489.

Pawar et al., 1995, "Differential gene expression in migrating renal epithelial cells after wounding", J Cell Physiol 165:556–565.

(List continued on next page.)

*Primary Examiner*—Geetha P. Bansal
(74) *Attorney, Agent, or Firm*—Pennie & Edmonds LLP (57) ABSTRACT

The invention relates to methods and compositions for the promotion of tissue repair. Specifically, compositions comprising heat shock proteins, including gp96, hsp90, and hsp70, uncomplexed or complexed noncovalently with antigenic molecules, are disclosed. Therapeutic methods for administering the hsp-containing compositions are disclosed. The disclosed methods are useful for promoting repair of tissues that were disrupted by a variety of causes including trauma (e.g., surgery, injury or burns) or disease or disorder (e.g., atherosclerosis and multiple sclerosis).

24 Claims, 6 Drawing Sheets

OTHER PUBLICATIONS

Schaffer et al., 1996, "Nitric oxide regulates wound healing", J Surg Res 63:237–240.

Schaffer et al., 1997, "Diabetes–impaired healing and reduced wound nitric oxide synthesis: a possible pathophysiologic correlation", Surgery 121:513–519.

Schaffer et al., 1997, "Nitric oxide metabolism in wounds", J Surg Res 71:25–31.

Vigh et al., 1997, "Bimoclomol: a nontoxic, hydroxylamine derivative with stress protein–inducing activity and cytoprotective effects", Nat Med 3:1150–1154.

Wang et al., 1996, "Macrophage–stimulating protein induces proliferation and migration of murine keratinocytes", Exp Cell Res 226:39–46.

Weller, 1997, "Nitric oxide—a newly discovered chemical transmitter in human skin", Br J Dermatol 137:665–672.

Wojciak and Crossan, 1994, "The effects of T cells and their products on in vitro healing of epitenon cell microwounds", Immunology 83:93–98.

Xue and Grossfeld, 1993, "Stress protein synthesis and accumulation after traumatic injury of crayfish CNS", Neurochem Res 18:209–218.

Yamasaki et al., 1998, "Reversal of impaired wound repair in iNOS–deficient mice by topical adenoviral–mediated iNOS gene transfer", J Clin Invest 101:967–971.

Zhou et al., 1996, "Expression of wound healing and stress-related proteins in keratoconus corneas", Curr Eye Res 15:1124–1131.

Zhu et al., 1996, "Human endothelial cells exposed to oxidized LDL express hsp70 only when proliferating", Arterioscler Thromb Vasc Biol 16:1104–1111.

COMPOSITIONS AND METHODS FOR PROMOTING TISSUE REPAIR USING HEAT SHOCK PROTEINS

This invention was made with government support under grant numbers CA44786 and CA64394 awarded by the National Institutes of Health. The government has certain rights in the invention.

1. INTRODUCTION

The present invention relates to methods for promoting tissue repair, including, but not limited to, wound healing. In the practice of treatment for tissue repair, compositions of complexes of heat shock/stress protein (hsps) including, but not limited to, gp96, hsp90, and hsp70, either alone or in combination with each other, noncovalently bound to antigenic molecules, are used to stimulate cells involved in the normal healing process. Alternatively, compositions containing uncomplexed stress proteins (i.e., free of antigenic molecules) are used to stimulate cells involved in the normal healing process.

2. BACKGROUND OF THE INVENTION

2.1. Process of Tissue Repair

The mechanisms of tissue repair involve the interaction of elements of both the coagulation cascade and the immune system. The process of tissue repair is divided into three phases: (1) inflammatory; (2) proliferative; and (3) remodelling. Although these phases are defined as distinct events, they occur as a continuum. The point at which tissue repair begins and ends is based largely upon macroscopic examination.

During the first phase of tissue repair, an acute inflammatory response with cellular migration occurs. Neutrophils predominate for the first 24–48 hours; macrophages become active by the third day. The neutrophils and macrophages phagocytose and digest pathologic organisms and tissue debris (Barbul et al., 1995, Wound Healing for the Otolaryngologist-Head and Neck Surg. 28:955–968).

Macrophage function is crucial in the process of tissue repair. In addition to decontaminating the wound, macrophages synthesize and secrete growth factors such as platelet derived growth factor (PDGF), fibroblast growth factor (FGF), transforming growth factor-alpha (TGF-α), and TGF-β which promote cell migration and proliferation and matrix formation (e.g., chemoattraction of fibroblasts into the wound edge).

Studies have identified a population of blood-borne cells, termed fibrocytes, that rapidly enter sites of tissue injury (Chesney et al., 1997, Proc. Natl. Acad. Sci. USA 94:6307–6312; Chesney and Bucala, 1997, Biochem. Soc. Transactions 25:520–524). Fibrocytes produce growth factors such as PDGF, FGF, TGF-β1; cytokines such as IL-1β and TNF-α; and matrix components.

Macrophage stimulating protein (MSP), a chemoattractant for peritoneal macrophages, has been shown to induce proliferation and migration of keratinocytes (Wang et al., 1996, Exp. Cancer Res. 226:39–46). Proliferation and differentiation of keratinocytes is important for normal skin function, wound healing, and tumor growth. Id. Thus, MSP may have implications for tissue repair of cutaneous wounds. Stimulation of macrophage function has also been demonstrated to have a beneficial effect on bowel anastomoses (Compton et al., 1996, Amer. Surg. 62:14–18).

The proliferative phase of tissue repair, typically lasting for 4–6 weeks, is characterized by fibroblast migration and neocapillary growth (angiogenesis). The fibroblasts synthesize collagen (as protocollagen, which is then hydroxylated to collagen). Capillary buds, originating in the venules at the edges of the wound, grow across the wound and supply nutrients and oxygen. Newly formed epithelial cells migrate onto the wound surface from the wound margins, resulting in the formation of a well-developed granulation tissue.

During the remodelling stage, cellular activity in the wound decreases. However, the wound continues to gain strength due to collagen cross-linking, remodelling and contraction. Studies have found that when cultured with specific antigen, fibrocytes function as antigen-presenting cells to specifically prime T lymphocytes (Chesney et al., 1997, Proc. Natl. Acad. Sci. USA 94:6307–6312; Chesney and Bucala, 1997, Biochem. Soc. Transactions 25:520–524). Studies suggest an indirect role for T lymphocytes in the wound healing process (administration of agents that enhance T lymphocyte function leads to increases in collagen deposition and wound strength) (Barbul et al., 1995, Wound Healing for the Otolaryngologist-Head and Neck Surg. 28:955968). Myofibroblasts exert a contractile force resulting in wound contraction, thereby decreasing the surface area of the wound, thus helping the wound to close.

2.2. Heat Shock Proteins

Hsps act as molecular chaperones and have been implicated in many processes, including: (1) promotion of folding and unfolding of nascent proteins; (2) participation and activation of a multi-enzymatic complex; (3) formation of complexes with hormone receptor, leading to activation; (4) intra- and intercompartmental transport of proteins; and (5) participation of folding of immunoglobulins (BiP).

Tissue repair encompasses healing of tissues disrupted by trauma (e.g., by surgery or injury) as well as disruption of tissues due to diseases including, but not limited to, atherosclerosis, and multiple sclerosis. Hsps are important for the maintenance of cell integrity during normal growth as well as during pathophysiological conditions (Vigh et al., 1997, Nature Medicine 3(10):1150–1154). Tissue injury, whether caused by surgery, trauma or disease, results in the induction of heat shock/stress proteins (hsps).

Levels of hsp 70 expression have been studied in wound healing. Oberringer et al. has demonstrated a correlation between well-healing wounds and overexpression of hsp 70, whereas chronic wounds exhibited weak or a complete lack of expression. (Oberringer et al., 1995, Biochem. Biophys. Res. Comm. 24(3):1009–1014). Zhu et al. has shown increased expression of hsp 70 in rapidly growing cells, such as those of lesion-prone areas of the vasculature, which may allow proliferating cells an increased chance of survival (Zhu et al., 1996, Arteriosclerosis, Thrombosis, and Vasc. Biol. 16(9) 1104–1111).

Oxidized low density lipoprotein (OxLDL), a causal factor in atherosclerosis, has been shown to induce expression of heat shock proteins (Zhu et al., 1996, Arteriosclerosis, Thrombosis, and Vasc. Biol. 16(9) 1104–1111). In multiple sclerosis, a demyelinating disease, remyelinization is achieved by the proliferation of oligodendrocytes. Studies have shown that heat shock proteins are up-regulated in astrocytes and oligodendrocytes during the course of multiple sclerosis (for review see, Boccaccio and Steinman, 1996, J. Neurosci. Res. 45:647–654).

There is a great need for compositions that promote tissue repair.

Citation or identification of any reference herein shall not be construed as an admission that such reference is available as prior art to the present invention.

3. SUMMARY OF THE INVENTION

The present invention relates to compositions and methods for promoting tissue repair. Methods for treatment comprise administering heat shock proteins (hsps), including but not limited to gp96, hsp90, hsp70, and combinations thereof. The hsps of the present invention may be noncovalently bound to antigenic molecules. The effectiveness of the hsp administration is not dependent on the organ or tissue type or cell from which the hsp was obtained. Accordingly, the treatment regimens disclosed are useful for the repair of a variety of tissues.

Particular compositions of the invention and their properties are described in the sections and subsections which follow. Doses of hsp administered for promoting tissue repair are provided. In addition, the invention provides pharmaceutical formulations for administration of the compositions in appropriate dosages. The invention also provides routes of administration of the compositions used for stimulation of tissue repair.

The examples presented in Section 6, below, demonstrate the use of compositions comprising gp96-peptide complexes in the stimulation of wound healing in a mouse model.

4. BRIEF DESCRIPTION OF THE FIGURES

FIG. 1A: liver derived gp96-peptide complex and LPS were each administered in a dose of 5 μg (or equivalent thereof) locally, i.e., near the wound site. FIG. 1B: liver derived gp96-peptide complex and LPS were each administered in a dose of 5 μg (or equivalent thereof) ventrally. FIG. 1C: liver derived gp96-peptide complex and LPS were each administered in a dose of 30 μg (or equivalent thereof) locally. FIG. 1D: liver derived gp96-peptide complex and LPS were each administered in a dose of 30 μg (or equivalent thereof) ventrally.

FIG. 2. Comparison graph of data depicted in FIGS. 1A–1D. Key: □=5 μg liver derived gp96-peptide complex administered locally; ■=30 μg liver derived gp96-peptide complex administered ventrally; ○=30 μg liver derived gp96-peptide complex administered locally; ●=5 μg liver derived gp96-peptide complex administered ventrally; Δ=30 μg equivalent LPS administered locally; ▲=5 μg equivalent LPS administered locally; ◇=5 μg equivalent LPS administered ventrally; ◆=30 μg equivalent LPS administered ventrally; ⊕=buffer administered locally; X=buffer administered ventrally.

FIGS. 3A–3F. Effect of gp96-peptide complex on the rate of wound healing in BALB/cJ mice. Days post-operation are plotted on the X-axis. Wound diameter (mm) is plotted on the Y-axis. For each experiment, mice receiving treatment with buffer alone served as controls. A wound having a diameter of 27 mm was inflicted on the dorsal skin (full-thickness). Mice were injected intradermally or subcutaneously with 200 μl of buffer or gp96-peptide complex derived from a methylcholanthrene-induced sarcoma (meth A derived gp96-peptide complex) on days 0, 1, 3, 8, and 11 post-operation. Wound diameter was measured (in two axes) on days 0, 1, 3, 8, 11, 14, and 17 post-operation. Buffer was used as the diluent. Results are presented as the mean diameter of 5 mice/group. Key: dotted line=buffer alone; solid line=meth A derived gp96-peptide complex. FIG. 3A: meth A derived gp96-peptide complex was administered intradermally in a dose of 1 μg, ventrally. FIG. 3B: meth A derived gp96-peptide complex was administered intradermally in a dose of 1 μg, locally. FIG. 3C: meth A derived gp96-peptide complex was administered subcutaneously, in a dose of 1 μg. FIG. 3D: meth A derived gp96-peptide complex was administered intradermally in a dose of 5 μg, ventrally. FIG. 3E: meth A derived gp96-peptide complex was administered intradermally in a dose of 5 μg, locally. FIG. 3F: meth A derived gp96-peptide complex was administered subcutaneously, in a dose of 5 μg.

5. DETAILED DESCRIPTION OF THE INVENTION

Methods and compositions for the stimulation of tissue repair are described. The invention provides treatment regimens which promote tissue repair. The treatment regimens comprise the administration of hsps, optionally complexed noncovalently with antigenic molecules.

Administration of hsps in accordance with the methods described below is a therapeutic modality for the stimulation of tissue repair and regeneration.

In accordance with the invention, hsps, either uncomplexed or complexed noncovalently with antigenic molecules, are administered to provide therapeutic treatment for the promotion of tissue repair.

"Antigenic molecule" as used herein refers to the peptides with which the hsps are endogenously associated in vivo as well as exogenous antigens/immunogens (molecules complexed with the hsps in vitro that are not from endogenous complexes with that hsp) or antigenic/immunogenic fragments and derivatives thereof.

The hsps of the present invention that can be used include but are not limited to, gp96, hsp90, and hsp70, either alone or in combination with each other. Preferably, the hsps are human hsps, although the hsps may be mammalian, murine, bovine, feline, bacterial, etc.

Heat shock proteins, which are also referred to interchangeably herein as stress proteins, useful in the practice of the instant invention can be selected from among any cellular protein that satisfies any one of the following criteria. A heat shock protein is characterized by having its intracellular concentration increase when a cell is exposed to a stressful stimuli, by being capable of binding other proteins or peptides, by being capable of releasing the bound proteins or peptides in the presence of adenosine triphosphate (ATP) or low Ph, or by having at least 35% homology with any cellular protein having any of the above properties.

The first stress proteins to be identified were the heat shock proteins (hsps). As their name implies, hsps are synthesized by a cell in response to heat shock. To date, three major families of hsp have been identified based on molecular weight. The families have been called hsp60, hsp70 and hsp90 where the numbers reflect the approximate molecular weight of the stress proteins in kilodaltons. Mammalian hsp90 and gp96 each are members of the hsp90 family. Many members of these families were found subsequently to be induced in response to other stressful stimuli including, but not limited to, nutrient deprivation, metabolic disruption, oxygen radicals, and infection with intracellular pathogens. (See Welch, May 1993, Scientific American 56–64; Young, 1990, Annu. Rev. Immunol. 8:401–420; Craig, 1993, Science 260:1902–1903; Gething, et al., 1992, Nature 355:33–45; and Lindquist, et al., 1988, Annu. Rev. Genetics 22:631–677). It is contemplated that hsps/stress proteins belonging to all of these three families can be used in the practice of the instant invention.

The major hsps can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch, et al., 1985, J. Cell. Biol. 101:1198–1211). In contrast, hsp90 and hsp60 proteins are abundant at normal temperatures in most, but not all, mammalian cells and are further induced by heat (Lai, et al., 1984, Mol. Cell. Biol. 4:2802–10; van Bergen en Henegouwen, et al., 1987, Genes Dev. 1:525–31).

Heat shock proteins are among the most highly conserved proteins in existence. For example, DnaK, the hsp70 from *E. coli* has about 50% amino acid sequence identity with hsp70 proteins from excoriates (Bardwell, et al., 1984, Proc. Natl. Acad. Sci. 81:848–852). The hsp60 and hsp90 families also show similarly high levels of intra families conservation (Hickey, et al., 1989, Mol. Cell. Biol. 9:2615–2626; Jindal, 1989, Mol. Cell. Biol. 9:2279–2283). In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

In a specific embodiment, the hsp used in accordance with the invention is a mammalian hsp. The hsp-peptide complexes of the invention include any complex containing an hsp and a peptide that is capable of stimulating tissue repair in a mammal. The peptides are preferably noncovalently associated with the hsp. Preferred complexes include, but are not limited to, hsp90-peptide complexes, hsp70-peptide complexes and hsp60-peptide complexes and combinations thereof. For example, an hsp called gp96 which is present in the endoplasmic reticulum of eukaryotic cells and is related to the cytoplasmic hsp90s (i.e., is a member of the hsp90 family) can be used to generate an effective therapeutic composition containing a gp96-peptide complex. In a specific embodiment, hsps complexed to the peptides with which they are endogenously associated are used, rather than hsps not so complexed, for purposes of convenience since the endogenous peptides copurify with the hsps.

Although the hsps can be allogeneic to the patient, in a preferred embodiment, the hsps are autologous to (derived from) the patient to whom they are administered. The hsps and/or antigenic molecules can be purified from natural sources, chemically synthesized, or recombinantly produced. The invention provides methods for determining doses for tissue repair therapy by evaluating the optimal dose of hsp, both unbound and noncovalently bound to peptide, in experimental models and extrapolating the data.

The therapeutic regimens and pharmaceutical compositions of the invention can be used with additional immune response enhancers or biological response modifiers including, but not limited to, interferon (IFN)-α, IFN-β, IFN-γ, interleukin (IL)-1, IL-2, IL-4, IL-5, IL-6, IL-15, or tumor necrosis factor, or with additional wound healing factors including, but not limited to, interferon (IFN)-β, IFN-γ, interleukin (IL)-1, IL-2, IL-4, IL-5, IL-15, tumor necrosis factor, flt-1 ligand, arginine, connective tissue growth factor, adenine nucleotides, adenosine, cyclic adenosine monophosphate, basic fibroblast growth factor, acidic fibroblast growth factor, tumor growth factor-α, tumor growth factor-β (1 and 2), vascular endothelial growth factor, epidermal growth factor (EGF) family (e.g., EGF, heparin-binding EGF, amphiregulin, betacellulin), platelet derived growth factor (PDGF) family (e.g., PDGF-A, PDGF-B, PDGF-AB), insulin-like growth factor (IGF) family (e.g., IGF-1, IGF-2), nitric oxide, macrophage-stimulating protein and macrophage-derived growth factor or other cytokines that affect wound healing (Podolsky, J., 1997 Gastroenterol. 32:122–126; Ankoma-Sey, et al., 1998, Oncogene 17:115–121; Wojciak and Crossan, 1994, Immunology, 83:93–9; Barbul, et al., 1990, Surgery 108:331–337; Kartha and Toback, 1992, J. Clin. Invest. 90:288–292; Bennett and Schultz, 1993, Am. J. Surg. 165:728–737; Bennett and Schultz, 1993, Am. J. Surg. 166:74–81; Oemar and Luscher, 1997, Arter. Throm. Vasc. Biol. 17:1483–1489; Yamasaki, et al., 1998, J. Clin. Invest. 101:967–971; Compton, et al., 1996, Am. Surg. 62:14–18; Wang, et al., 1996, Exp. Cell Res. 226:39–46). In accordance with this aspect of the invention the hsp, either complexed or uncomplexed with antigenic molecules, is administered in combination with or sequentially to, one or more of the foregoing cytokines, proteins, nucleotides or growth factors as well as any other biological response modifier or wound healing factor known in the art.

Accordingly, the invention provides methods of promoting tissue repair, including wound healing, in an individual comprising administering a composition comprising hsps, either uncomplexed or complexed noncovalently with antigenic molecules, which elicits stimulation of cells involved in the process of tissue repair (including, but not limited to macrophages, oligodendrocytes, T cells).

5.1. Target Tissues

Tissues that can be treated by the methods of the present invention include, but are not limited to, lesioned or injured tissues disrupted by trauma (e.g., surgery, injury, burns) or disease (e.g., atherosclerosis and multiple sclerosis).

Lesions which may be treated according to the present invention include but are not limited to the following lesions:

(i) traumatic lesions, including lesions caused by physical injury or associated with surgery;

(ii) ischemic lesions, in which a lack of oxygen results in cell injury or death, e.g., myocardial or cerebral infarction or ischemia, or spinal cord infarction or ischemia;

(iii) malignant lesions, in which cells are destroyed or injured by malignant tissue;

(iv) infectious lesions, in which tissue is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which tissue is destroyed or injured as a result of a degenerative process, including but not limited to nervous system degeneration associated with Parkinson's disease, Alzheimer's disease, Huntington's chorea, or amyotrophic lateral sclerosis;

(vi) lesions associated with nutritional diseases or disorders, in which tissue is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) lesions associated with systemic diseases including but not limited to diabetes or systemic lupus erythematosus;

(viii) lesions caused by toxic substances including alcohol, lead, or other toxins; and (ix) demyelinated lesions of the nervous system, in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

The methods of the present invention can be used to promote tissue repair by stimulating cells of the immune system, e.g., macrophages, T cells involved in the mechanism of tissue repair and regeneration.

5.2. Obtaining Therapeutic Compositions for Promotion of Tissue Repair

The hsps used in accordance with the invention can be complexed with antigenic molecules (e.g., peptides), or uncomplexed. Whether complexed or not, the hsps can be native (non-recombinant) or recombinant. The antigenic molecules can be endogenous, i.e., naturally associated with hsp intracellularly. Alternatively, the antigenic molecules can be exogenous, i.e., not naturally occurring in a noncovalent complex with hsps, or eluted from a cellularly derived noncovalent complex with hsps and reconstituted with other hsps in vitro. Preferably, the hsp, or complex, as the case may be, is used in purified form, preferably to homogeneity as viewed on a polyacrylamide gel, or to at least 60%, 70%, 80%, or 90% of total protein.

The hsp-peptide complexes can be isolated as such from cells wherein the hsp and antigenic molecule are produced. Hsps or exogenous antigenic molecules can be produced in the cell by recombinant expression of a gene encoding that component (either hsp or antigenic molecule), or can be isolated from native sources. The hsps and exogenous antigenic molecule components can be produced and isolated independently and complexed in vitro. Alternatively, complexes of hsps and endogenous peptides can be isolated from cells. In a preferred embodiment for in vitro complexing of hsps and exogenous antigenic molecules, the hsp component is first isolated from cells as a complex, and then purified away from the noncovalently bound endogenous peptide with which it is complexed, prior to complexing in vitro with the exogenous antigenic molecule of interest. Alternatively, the hsp component is first isolated from cells as a complex, and then the noncovalently bound endogenous peptide with which it is complexed is exchanged in vitro with the exogenous antigenic molecule of interest.

Accordingly, the protocols described herein can be used to isolate and produce purified hsps or purified complexes of hsps and antigenic molecules.

Uncomplexed endogenous hsps and endogenous hsps complexed with antigenic molecules can be isolated from any eukaryotic cells, including but not limited to, tissues, isolated cells, and immortalized eukaryotic cell lines. The tissue source need not be the same as the tissue which is targeted by the subject repair response. Suitable source tissues include, but are not limited to purified lymphocytes, liver, spleen, or any organ of mammalian or non-mammalian origin. Source tissue may be autologous (i.e., from the same individual) or non-autologous. Non-autologous source tissue may be obtained from a cadaver. In an embodiment, uncomplexed endogenous hsps and endogenous hsps complexed with antigenic molecules can be isolated from tumor cells. In another embodiment, the hsp or hsp-peptide complex is isolated from tissue excised from a human.

Alternatively, the hsps can be produced by recombinant DNA technology using techniques well known in the art. These methods are described in detail in Section 5.2.2, below.

Peptides derived from either a naturally expressed protein (i.e., native peptide) or from a recombinantly expressed protein can be isolated by first isolating the corresponding hsp-peptide complex and then eluting the peptide. Methods for eluting noncovalently bound peptide from the hsp-peptide complex are described in Section 5.2.4, below. Peptides can also be produced synthetically and subsequently complexed with hsps in vitro.

Methods for complexing hsps with antigenic molecules in vitro are described in Section 5.2.5, below.

The hsps to be used therapeutically, alone or complexed, need not be isolated from a sample from the patient to which they are then to be administered to treat disrupted tissue, i.e., the hsps (and antigenic molecules) can be autologous or non-autologous.

5.2.1. Preparation of Hsp-Peptide Complexes

The methods described in Sections 5.2.1.1–5.2.1.3, below, can be used to isolate hsps complexed with antigenic molecules from cells, preferably from cells expressing non-recombinant hsps, although cells expressing recombinant hsps may also be used. In a specific embodiment, hsps complexed with peptides can be isolated from tumor cells. In another embodiment, hsps complexed with peptides are isolated from non-malignant cells. These same methods may also be used to prepare purified hsp, by removing the endogenous antigenic molecules from the isolated complexes by methods described in Section 5.2.3, below.

5.2.1.1. Preparation and Purification of gp96-peptide Complexes

A procedure that can be used, presented by way of example and not limitation, is as follows:

A pellet of eukaryotic cells (e.g., from liver, spleen, or any other suitable organ) is resuspended in 3 volumes of buffer consisting of 30 mM sodium bicarbonate buffer (Ph 7.5) and 1 mM PMSF and the cells allowed to swell on ice 20 minutes. The cell pellet then is homogenized in a Dounce homogenizer (the appropriate clearance of the homogenizer will vary according to each cell type) on ice until >95% cells are lysed.

The lysate is centrifuged at 1,000×g for 10 minutes to remove unbroken cells, nuclei and other debris. The supernatant from this centrifugation step then is recentrifuged at 100,000×g for 90 minutes. The gp96-peptide complex can be purified either from the 100,000×g pellet or from the supernatant.

When purified from the supernatant, the supernatant is diluted with equal volume of 2× lysis buffer and the supernatant mixed for 2–3 hours at 40° C. with Con A-Sepharose® (Pharmacia, Inc., Sweden) equilibrated with PBS containing 2 mM $Ca^{2+}$ and 2 mM $Mg^{2+}$. Then, the slurry is packed into a column and washed with 1× lysis buffer until the $OD_{280}$ drops to baseline. Then, the column is washed with 1/3 column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure, however this depends upon the cell type and the tissue-to-lysis buffer ratio used. Then the sample is applied to a Mono QO FPLC ion-exchange chromatographic column (Pharmacia, Inc., Piscataway, N.J.) equilibrated with a buffer containing 5 mM sodium phosphate, pH 7. The proteins are then eluted from the column with a 0–1M NaCl gradient. The gp96 fraction elutes between 400 mM and 550 mM NaCl.

The procedure, however, can be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose® purification after the Con A purification step but before the Mono Q® FPLC step.

In the first optional step, the supernatant resulting from the 100,000×g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose® and the procedure followed as before.

In the second optional step, the gp96 containing fractions eluted from the Con A column are pooled and the buffer exchanged for 5 mM sodium phosphate buffer, pH 7, 300 mM NaCl by dialysis, or preferably by buffer exchange on a Sephadex G25 column (Pharmacia, Inc., Sweden). After buffer exchange, the solution is mixed with DEAE-Sepharose® previously equilibrated with 5 mM sodium phosphate buffer, pH 7, 300 mM NaCl. The protein solution and the beads are mixed gently for 1 hour and poured into a column. Then, the column is washed with 5 mM sodium phosphate buffer, pH 7, 300 mM NaCl, until the absorbance at 280 nM drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM . The resulting material then is applied to the Mono Q® FPLC column (Pharmacia) equilibrated with 5 mM sodium phosphate buffer, pH 7 and the protein that binds to the Mono Q® FPLC column (Pharmacia) is eluted as described before.

It is appreciated, however, that one skilled in the art can assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000×g pellet, the pellet is suspended in 5 volumes of PBS containing either 1% sodium deoxycholate or 1% octyl glucopyranoside (but without the $Mg^{2+}$ and $Ca^{2+}$) and incubated on ice for 1 hour. The suspension is centrifuged at 20,000×g for 30 minutes and the resulting supernatant dialyzed against several changes of PBS (also without the $Mg^{2+}$ and $Ca^{2+}$) to remove the detergent. The dialysate is centrifuged at 100,000×g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000×g supernatant, see above.

The gp96-peptide complexes can be purified to apparent homogeneity using this procedure. About 10–20 μg of gp96-peptide complex can be isolated from 1 g cells/tissue.

5.2.1.2. Preparation and Purification of Hsp 70-peptide Complexes

The purification of hsp70-peptide complexes has been described previously, see, for example, Udono et al., 1993, *J. Exp. Med.* 178:1391–1396. A procedure that can be used, presented by way of example but not limitation, is as follows:

Initially, cells (e.g., from liver, spleen, or any other suitable organ) are suspended in 3 volumes of 1× lysis buffer consisting of 5 mM sodium phosphate buffer, pH 7, 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells can be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000×g for 10 minutes to remove unbroken cells, nuclei and other cellular debris. The resulting supernatant is recentrifuged at 100,000×g for 90 minutes, the supernatant harvested and then mixed with Con A Sepharose® equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× lysis buffer prior to mixing with Con A Sepharose®. The supernatant is then allowed to bind to the Con A Sepharose® for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q® FPLC column equilibrated in 20 mM Tris-Acetate pH 7.5, 20 mM NaCl, 0.1 mM EDTA and 15 mM 2-mercaptoethanol. The column is then developed with a 20 mM to 500 mM NaCl gradient and eluted fractions fractionated by sodium dodecyl sulfate-polyacrylamide gel electrophoresis (SDS-PAGE) and characterized by immunoblotting using an appropriate anti-hsp70 antibody (such as from clone N27F3-4, from StressGen, Victoria, British Columbia, Canada).

Fractions strongly immunoreactive with the anti-hsp70 antibody are pooled and the hsp70-peptide complexes precipitated with ammonium sulfate; specifically with a 50%–70% ammonium sulfate cut. The resulting precipitate is then harvested by centrifugation at 17,000 rpm (SS34

Sorvall rotor) and washed with 70% ammonium sulfate. The washed precipitate is then solubilized and any residual ammonium sulfate removed by gel filtration on a Sephadex G25 column (Pharmacia). If necessary the hsp70 preparation thus obtained can be repurified through the Mono Q® FPLC column as described above.

The hsp70-peptide complex can be purified to apparent homogeneity using this method. Typically 1 mg of hsp70-peptide complex can be purified from 1 g of cells/tissue.

The present invention further describes a rapid method for purification of hsp70-peptide complexes. This improved method comprises contacting cellular proteins with ADP or a nonhydrolyzable analog of ATP affixed to a solid substrate, such that hsp70 in the lysate can bind to the ADP or nonhydrolyzable ATP analog, and eluting the bound hsp70. A preferred method uses column chromatography with ADP affixed to a solid substratum (e.g., ADP-agarose). The resulting hsp70 preparations are higher in purity and devoid of contaminating peptides. The hsp70 yields are also increased significantly by about more than 10 fold. Alternatively, chromatography with nonhydrolyzable analogs of ATP, instead of ADP, can be used for purification of hsp70-peptide complexes.

By way of example but not limitation, purification of hsp70-peptide complexes by ADP-agarose chromatography is carried out as follows:

500 million cells (e.g., from liver, spleen, or any other suitable organ) are homogenized in hypotonic buffer and the lysate is centrifuged at 100,000×g for 90 minutes at 4° C. The supernatant is applied to an ADP-agarose column. The column is washed in buffer and is eluted with 5 column volumes of 3 mM ADP. The hsp70-peptide complexes elute in fractions 2 through 10 of the total 15 fractions which elute. The eluted fractions are analyzed by SDS-PAGE. The hsp70-peptide complexes can be purified to apparent homogeneity using this procedure.

5.2.1.3. Preparation and Purification of Hsp 90-peptide Complexes

A procedure that can be used to prepare hsp90-peptide complexes, presented by way of example and not limitation, is as follows:

Initially, cells (e.g., from liver, spleen, or any other convenient organ) are suspended in 3 volumes of 1×Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells can be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000×g for 10 minutes to remove unbroken cells, nuclei and other cellular debris. The resulting supernatant is recentrifuged at 100,000×g for 90 minutes, the supernatant harvested and then mixed with Con A Sepharose® equilibrated with PBS containing 2 mM $Ca^{2+}$ and 2 mM $Mg^{2+}$. When the cells are lysed by mechanical shearing the supernatant is diluted with an equal volume of 2×Lysis buffer prior to mixing with Con A Sepharose®. The supernatant is then allowed to bind to the Con A Sepharose® for 2–3 hours at 4° C. The material that fails to bind is harvested and dialyzed for 36 hours (three times, 100 volumes each time) against 20 mM sodium phosphate, pH 7.4, 1 mM EDTA, 250 mM NaCl, 1 mM PMSF. Then the dialyzate is centrifuged at 17,000 rpm (Sorvall SS34 rotor) for 20 minutes. Then the resulting supernatant is harvested and applied to a Mono Q® FPLC column equilibrated with a buffer containing 20 mM sodium phosphate, pH 7.4, 1 mM EDTA, 250 mM NaCl, 1 mM PMSF. The proteins are then eluted with a salt gradient of 200 mM to 600 mM NaCl.

The eluted fractions are fractionated by SDS-PAGE and fractions containing the hsp90-peptide complexes identified by immunoblotting using an anti-hsp90 antibody such as 3G3 (Affinity Bioreagents). Hsp90-peptide complexes can be purified to apparent homogeneity using this procedure. Typically, 150–200 µg of hsp90-peptide complex can be purified from 1 g of cells/tissue.

5.2.2. Recombinant Production of Hsps and Hsp-Peptide Complexes

Many genes encoding hsps have been cloned and sequenced, including, for example, human hsp70 (GenBank Accession Nos. M11717 and M15432; see also Hunt and Morimoto, 1985, Proc. Natl. Acad. Sci. USA 82: 6455–6459), human hsp90 (GenBank Accession No. X15183; see also Yamazaki et al., 1989, Nucleic Acids Res. 17: 7108), and human gp96 (GenBank Accession No. M33716; see also Maki et al., 1990, Proc. Natl. Acad. Sci. USA 87: 5658–5662).

The hsps, alone or complexed to antigenic molecules, can be produced by recombinant DNA technology using techniques well known in the art. Methods which are well known to those skilled in the art can be used to construct expression vectors containing hsp coding sequences and/or antigenic molecule coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra.

A variety of host-expression vector systems can be utilized to express the hsp genes. These include but are not limited to microorganisms such as bacteria (e.g., E. coli, B. subtilis) transformed with recombinant bacteriophage DNA, plasmid DNA or cosmid DNA expression vectors containing the hsp coding sequence; yeast (e.g. Saccharomyces, Pichia) transformed with recombinant yeast expression vectors containing the hsp coding sequence; insect cell systems infected with recombinant virus expression vectors (e.g., baculovirus) containing the hsp coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the hsp coding sequence; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, for example, vectors which direct the expression of high levels of fusion protein products that are readily purified may be desirable. Such vectors include, but are not limited, to the E. coli expression vector pUR278 (Ruther et al., 1983, EMBO J. 2:1791), in which the hsp coding sequence can be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned hsp gene protein can be released from the GST moiety.

In an insect system, *Autographa californica* nuclear polyhedrosis virus (AcNPV) is used as a vector to express foreign genes. The virus grows in *Spodoptera frugiperda* cells. The hsp gene can be cloned individually into non-essential regions (for example the polyhedrin gene) of the virus and placed under control of an AcNPV promoter (for example the polyhedrin promoter). Successful insertion of the hsp coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol. 46: 584; Smith, U.S. Pat. No. 4,215,051).

In mammalian host cells, a number of viral-based expression systems are preferably utilized. In cases where an adenovirus is used as an expression vector, the hsp coding sequence can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing hsps in infected hosts. (See, e.g., Logan & Shenk, 1984, Proc. Natl. Acad. Sci. USA 81:3655–3659). Specific initiation signals may also be required for efficient translation of inserted hsp coding sequence. These signals include the ATG initiation codon and adjacent sequences. The efficiency of expression can be enhanced by the inclusion of appropriate transcription enhancer elements, transcription terminators, etc. (see Bittner et al., 1987, Methods in Enzymol. 153:516–544).

In addition, a host cell strain can be chosen which modulates the expression of the inserted sequences, or modifies and processes the hsp in the specific fashion desired. For example, choosing a system that allows for appropriate glycosylation is especially important in the case of gp96. Different host cells have characteristic and specific mechanisms for the post-translational processing and modification of proteins such as glycosylation. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

In a preferred embodiment for recombinant expression of hsps, the histidine-nickel (his-Ni) tag system is used (Janknecht et al., 1991, Proc. Natl. Acad. Sci. USA 88: 8972–8976). In the his-Ni system, the hsp is expressed in human cell lines as a fusion protein which can be readily purified in a non-denatured form. In this system, the gene of interest (i.e., the hsp gene) is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Kits for expressing isolating proteins using the his-Ni system are commercially available from Invitrogen®, San Diego, Calif.

Alternatively, recombinant hsps produced in eukaryotic hosts cells as described in this section, above, can be purified according to the respective methods detailed in Section 5.2.1, above.

5.2.3. Preparation and Purification of Uncomplexed hsps

The following methods can be used to obtain uncomplexed hsps, i.e., hsps that are substantially free of noncovalently bound antigenic molecules such as peptides. In a specific embodiment, the hsps can be administered in their uncomplexed form in accordance with the invention for the repair of tissues. In addition, the uncomplexed hsps can be used to design hsp-antigenic molecule complexes by complexing them in vitro with antigenic molecules of interest, as described in Section 5.2.5, below.

5.2.3.1. General Methods

Methods which can be used to separate the hsp and antigenic molecule components of the hsp-antigenic molecule complexes from each other, include, but are not limited to, treatment of the complexes with low pH. The low pH treatment methods described in this section, below, can be used for hsp70, hsp90, or gp96. An alternative method which is preferred for isolating hsp70 from hsp-antigenic molecule complexes is provided in Section 5.2.3.2.

By way of example but not limitation, to elute the noncovalently bound antigenic molecule using low pH, acetic acid or trifluoroacetic acid is added to the purified hsp-antigenic molecule complex to give a final concentration of 10% (vol/vol) and the mixture incubated at room temperature or in a boiling water bath or any temperature in between, for 10 minutes (See, Van Bleek, et al., 1990, *Nature* 348:213–216; and Li, et al., 1993, *EMBO Journal* 12:3143–3151). The resulting samples are centrifuged through a Centricon® 10 assembly. The high and low molecular weight fractions are recovered. The remaining large molecular weight hsp70-peptide complexes can be reincubated in low pH to remove any remaining peptides. The resulting higher molecular weight fractions containing hsp are pooled and concentrated.

5.2.3.2. Preferred Method for Preparation and Purification of Uncomplexed Hsp 70

Preferably, the hsp70-peptide complex is purified as described above in Section 5.2.1.2. Once the hsp70-peptide complex is purified, the peptide is eluted from the hsp70 by either of the following two preferred methods. More preferably, the hsp70-peptide complex is incubated in the presence of ATP. Alternatively, the hsp70-peptide complex is incubated in a low pH buffer, as described in Section 5.2.2, above.

Briefly, the complex is centrifuged through a Centricon® 10 assembly (Millipore) to remove any low molecular weight material loosely associated with the complex. The large molecular weight fraction can be removed and analyzed by SDS-PAGE while the low molecular weight can be analyzed by HPLC as described below. In the ATP incubation protocol, the stress protein-peptide complex in the large molecular weight fraction is incubated with 10 mM ATP for 30 minutes at room temperature.

The resulting samples are centrifuged through a Centricon® 10 assembly as mentioned previously. The high and low molecular weight fractions are recovered. The remaining large molecular weight hsp70-peptide complexes can be reincubated with ATP to remove any remaining peptides.

The resulting higher molecular weight fractions containing hsp70 are pooled and concentrated.

5.2.4. Isolation of Antigenic Components

The methods described in Section 5.2.3, above, which can be used to isolate hsps from complexes with antigenic molecules, can similarly be used to isolate peptides and/or antigenic components from cells which may contain potentially useful antigenic determinants. Once the hsps and antigenic molecules are separated from each other into separate fractions, the fractions containing the antigenic molecules can be pooled and processed further, as described below. Once isolated, the amino acid sequence of each antigenic peptide can be determined using conventional amino acid sequencing methodologies. Such antigenic molecules can then be produced by chemical synthesis or recombinant methods, purified, and complexed to hsps in vitro.

Similarly, it has been found that potentially immunogenic peptides may be eluted from MHC-peptide complexes using techniques well known in the art (Falk, K. et al., 1990, Nature 348:248–251; Elliott, T., et al., 1990, Nature 348:195–197; Falk, K., et al., 1991, Nature 351:290–296).

Thus, potentially immunogenic or antigenic peptides can be isolated from either stress protein-peptide complexes or MHC-peptide complexes for use subsequently as antigenic molecules, by complexing in vitro to hsps. Exemplary protocols for isolating peptides and/or antigenic components from either of the these complexes are set forth below in Sections 5.2.4.1 and 5.2.4.2.

5.2.4.1. Peptides From Stress Protein-Peptide Complexes

The methods detailed in Section 5.2.3, above, can be used to elute the peptide from a stress protein-peptide complex. One approach involves incubating the stress protein-peptide complex in the presence of ATP. The other approach involves incubating the complexes in a low pH buffer.

Briefly the complex of interest is centrifuged through a Centricon® 10 assembly (Millipore) to remove any low molecular weight material loosely associated with the complex. The large molecular weight fraction can be removed and analyzed by SDS-PAGE while the low molecular weight can be analyzed by HPLC as described below. In the ATP incubation protocol, the stress protein-peptide complex in the large molecular weight fraction is incubated with 10 mM ATP for 30 minutes at room temperature. In the low pH protocol, acetic acid or trifluoroacetic acid (TFA) is added to the stress protein-peptide complex to give a final concentration of 10% (vol/vol) and the mixture incubated at room temperature or in a boiling water bath or any temperature in between, for 10 minutes (See, Van Bleek, et al., 1990, Nature 348:213–216; and Li, et al., 1993, EMBO Journal 12:3143–3151).

The resulting samples are centrifuged through a Centricon® 10 assembly as mentioned previously. The high and low molecular weight fractions are recovered. The remaining large molecular weight stress protein-peptide complexes can be reincubated with ATP or low pH to remove any remaining peptides.

The resulting lower molecular weight fractions are pooled, concentrated by evaporation and dissolved in 0.1% TFA. The dissolved material is then fractionated by reverse phase high pressure liquid chromatography (HPLC) using for example a VYDAC® C18 reverse phase column (Separations Group, Inc., Hesperia, Calif.) equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by $OD_{210}$ and the fractions containing the peptides collected.

5.2.4.2. Peptides from MHC-peptide Complexes

The isolation of potentially immunogenic peptides from MHC molecules is well known in the art and so is not described in detail herein (See, Falk, et al., 1990, Nature 348:248–251; Rotzsche, at al., 1990, Nature 348:252–254; Elliott, et al., 1990, Nature 348:191–197; Falk, et al., 1991, Nature 351:290–296; Demotz, et al., 1989, Nature 343:682–684; Rotzsche, et al., 1990, Science 249:283–287, the disclosures of which are incorporated herein by reference).

Briefly, MHC-peptide complexes can be isolated by a conventional immunoaffinity procedure. The peptides then can be eluted from the MHC-peptide complex by incubating the complexes in the presence of about 0.1% TFA in acetonitrile. The eluted peptides can be fractionated and purified by reverse phase HPLC, as before.

The amino acid sequences of the eluted peptides can be determined either by manual or automated amino acid sequencing techniques well known in the art. Once the amino acid sequence of a potentially protective peptide has been determined the peptide can be synthesized in any desired amount using conventional peptide synthesis or other protocols well known in the art.

5.2.4.3. Synthetic Production of Peptides

Peptides having the same amino acid sequence as those isolated above, or a different amino acid sequence, can be produced by recombinant DNA technology using methods described in Section 5.2.2, above, or can be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an a-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads. The N-α-protecting group is then removed. The deprotected α-amino group is coupled to the activated a-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.2.5. In vitro Production of Stress Protein-Antigenic Molecule Complexes

In an embodiment in which complexes of hsps and the peptides with which they are endogenously associated in vivo are not employed, and it is desired to use hsp-antigenic molecule complexes, complexes of hsps to antigenic molecules are produced in vitro. As will be appreciated by those skilled in the art, the peptides either isolated by the aforementioned procedures or chemically synthesized or recombinantly produced can be reconstituted with a variety of purified natural, recombinant, or chemically synthesized stress proteins in vitro to generate immunogenic noncovalent stress protein-antigenic molecule complexes. Alternatively, exogenous antigens or antigenic/immunogenic fragments or derivatives thereof can be noncovalently complexed to stress proteins for use in the methods of the invention. A preferred, exemplary protocol for noncovalently complexing a stress protein and an antigenic molecule in vitro is discussed below.

Prior to complexing, the hsps are pretreated with ATP or low pH to remove any peptides that may be associated with the hsp of interest. When the ATP procedure is used, excess ATP is removed from the preparation by the addition of apyranase as described by Levy, et al., 1991, Cell 67:265–274. When the low pH procedure is used, the buffer is readjusted to neutral pH by the addition of pH modifying reagents.

The antigenic molecules (1 $\mu$g) and the pretreated hsp (9 $\mu$g) are admixed to give an approximately 5 antigenic molecule: 1 stress protein molar ratio. Then, the mixture is incubated for 15 minutes to 3 hours at 40 to 45° C. in a suitable binding buffer such as one containing 20 mM sodium phosphate, pH 7.2, 350 mM NaCl, 3 mM MgCl$_2$ and 1 mM phenyl methyl sulfonyl fluoride (PMSF). The preparations are centrifuged through a Centricon® 10 assembly (Millipore) to remove any unbound peptide. The association of the peptides with the stress proteins can be assayed by SDS-PAGE. This is the preferred method for in vitro complexing of peptides isolated from MHC-peptide complexes of peptides disassociated from endogenous hsp-peptide complexes.

In an alternative embodiment of the invention, preferred for producing complexes of hsp70 to exogenous antigenic molecules such as peptides, 5–10 micrograms of purified hsp is incubated with equimolar quantities of the antigenic molecule in 20 mM sodium phosphate buffer pH 7.5, 0.5M NaCl, 3 mM MgCl$_2$ and 1 mM ADP in a volume of 100 microliter at 37° C. for 1 hr. This incubation mixture is further diluted to 1 ml in phosphate-buffered saline.

In an alternative embodiment of the invention, preferred for producing complexes of hsp90 to peptides, 5–10 micrograms of purified hsp90 is incubated with equimolar or excess quantities of the antigenic peptide in a suitable buffer such as one containing 20 mM sodium phosphate buffer pH 7.5, 0.5M NaCl, 3 nM MgCl$_2$ at 60–65° C. for 5–20 min. Alternatively, equimolar or excess quantities of peptide (e.g., exogenous peptide) are added to purified hsp90-peptide (endogenous) complex, such that the exogenous peptide is exchanged for the endogenous peptide. In either case, the incubation mixture is allowed to cool to room temperature and centrifuged one or more times if necessary, through a Centricon® 10 assembly (Millipore) to remove any unbound peptide.

In an alternative embodiment of the invention, preferred for producing complexes of gp96 with peptides, 100–300 nM purified peptide is added to 100 nM purified gp96. Alternatively, 100–300 nM peptide (e.g., exogenous peptide) is added to purified gp96-peptide (endogenous) complex, such that the exogenous peptide is exchanged for the endogenous peptide. In either case, the mixture is incubated in a binding buffer consisting of 20 mM HEPES, pH 7.2, 20 mM NaCl, and 2 mM MgCl$_2$ at 60° C. for 10 min. and allowed to cool to room temperature for an additional 10 min. After centrifugation, the sample is incubated for 30 min. at room temperature. Free peptide is removed completely using a microcon 50 (Amicon, Inc.).

Once complexes have been isolated, they can be characterized further for tolerogenicity in animal models using the preferred administration protocols and excipients discussed below.

5.3. Dosage Regimens

Hsps and hsp-antigenic molecule complexes are administered to mammalian subjects, e.g., primates, dogs, cats, mice, rats, horses, cows, pigs, etc., preferably humans, in doses in a range of about 1 $\mu$g to about 5000 $\mu$g, preferably in a range of about 1 $\mu$g to about 1500 $\mu$g. In mammals, a range of about 30 $\mu$g to about 500 $\mu$g, preferably intradermally, with about 5 $\mu$g to about 100 $\mu$g intradermally even more preferred. As demonstrated in the example in Section 6, below, an effective dose for promotion of wound healing in a mouse model is 30 $\mu$g gp96 administered intradermally for mice of average mass of 20–25 g.

Methods of introduction include but are not limited to intradermal, intramuscular, intraperitoneal, intravenous, subcutaneous, intranasal, epidural, and oral routes. The hsps or complexes may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In a specific embodiment, the hsp compositions are administered, either intradermally or subcutaneously, with sites of administration varied sequentially. For example, and not by way of limitation, the doses recited above are given once weekly for a period of about 4 to 6 weeks, and the mode of administration is varied with each administration. Each site of administration may be varied sequentially. Thus, by way of example and not limitation, the injections can be given, either intradermally or subcutaneously, locally (i.e., near the wound site) or at a site distant from the site of damage. The same site can be repeated after a gap of one or more injections. Also, split injections can be given. Thus, for example, half the dose can be given in one site and the other half in another site on the same day.

After 4–6 weeks, further injections are preferably given at two-week intervals over a period of time of one month. Later injections can be given monthly. The pace of later injections can be modified, depending upon the patient's clinical progress and responsiveness to the therapy. Alternatively, the mode of administration is sequentially varied, e.g., weekly administrations are given in sequence intradermally or subcutaneously.

5.4. Formulation

The uncomplexed hsps or hsps complexed with antigenic molecules, in accordance with the invention, can be formulated into pharmaceutical preparations for administration to mammals, preferably humans, for promotion of tissue repair. Compositions comprising a compound of the invention formulated in a compatible pharmaceutical carrier can be prepared, packaged, and labelled for and promotion of tissue repair, such as wound healing or regeneration of tissue damaged by disease, including but not limited to multiple sclerosis or atherosclerosis.

If the complex is water-soluble, then it can be formulated in an appropriate buffer, for example, phosphate buffered saline or other physiologically compatible solutions. Alternatively, if the resulting complex has poor solubility in aqueous solvents, then it can be formulated with a non-ionic surfactant such as Tween, or polyethylene glycol. Thus, the compounds and their physiologically acceptable solvates can be formulated for administration by inhalation or insufflation (either through the mouth or the nose) or oral, buccal, parenteral, rectal administration.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art.

Preparations for oral administration can be suitably formulated to give controlled release of the active compound.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can be formulated into creams, lotions, ointments or tinctures, e.g., containing conventional bases, such as hydrocarbons, petrolatum, lanolin, waxes, glycerin, or alcohol. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

The invention also provides kits for carrying out the therapeutic regimens of the invention. Such kits comprise in one or more containers therapeutically effective amounts of the hsp or hsp-antigenic molecule complexes in pharmaceutically acceptable form. The hsp or hsp-antigenic molecule complex in a vial of a kit of the invention can be in the form of a pharmaceutically acceptable solution, e.g., in combination with sterile saline, dextrose solution, or buffered solution, or other pharmaceutically acceptable sterile fluid. Alternatively, the complex can be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of hsp or hsp-antigenic molecule complexes by a clinician or by the patient.

5.5. Promotion of Tissue Repair

The compositions and formulations described above in Sections 5.2 and 5.4 can be used to stimulate the repair of tissues damaged by lesions, trauma (e.g. injury, surgery or burn) or disease including, but not limited to, multiple sclerosis and atherosclerosis. Administration of hsp-based compositions can be used to stimulate cells of the immune system that are involved in the process of tissue repair.

Lesions which may be treated according to the present invention including but not limited to the following:

(i) traumatic lesions, including lesions caused by physical injury or associated with surgery;

(ii) ischemic lesions, in which a lack of oxygen results in cell injury or death, e.g., is myocardial or cerebral infarction or ischemia, or spinal cord infarction or ischemia;

(iii) malignant lesions, in which cells are destroyed or injured by malignant tissue;

(iv) infectious lesions, in which tissue is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which tissue is destroyed or injured as a result of a degenerative process, including but not limited to nervous system degeneration associated with Parkinson's disease, Alzheimer's disease, Huntington's chorea, or amyotrophic lateral sclerosis;

(vi) lesions associated with nutritional diseases or disorders, in which tissue is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) lesions associated with systemic diseases including but not limited to diabetes or systemic lupus erythematosus;

(viii) lesions caused by toxic substances including alcohol, lead, or other toxins; and (ix) demyelinated lesions of the nervous system, in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

5.5.1. Methods of Treatment Based on Administration of Hsps

The example presented in Section 6, below, details the use in accordance with the methods of the invention of the hsp gp96 in therapy in an experimental model for wound healing.

In accordance with the invention, the hsp-based compositions and formulations described in Sections 5.2 and 5.4, above, are administered to treat damage to tissues resulting from trauma or disease. In a specific embodiment, administration can be carried out both prior and subsequent to trauma (planned trauma, e.g., surgery), in 2 to 4 doses each one week apart, at least one of which precedes trauma.

5.6. Monitoring of Effects During Therapy

The effects/efficacy of treatment of damaged tissue according to the present invention can be detected, for example, on the level of the molecular and cellular agents involved in the immune response (e.g., macrophages, oligodendrocytes, T cells) or on the level of an affected tissue including, but not limited to, stimulation of macrophages to secrete growth factors, presence of fibrocytes, migration of fibroblasts to the wound site, synthesis and cross-linking of collagen, and decrease in wound size.

6. EXAMPLE

Administration of Liver Derived GP96-Peptide Complex Accelerates Wound Healing

The results described below demonstrate the function of the hsp gp96-peptide complex as a stimulator of tissue repair. Administration of gp96-peptide complex accelerated the wound healing process. Further, the results below demonstrate that lipopolysaccharide (LPS) adversely affected wound healing.

These results demonstrate that hsps administered in accordance with the invention are effective agents for the promotion of tissue repair.

6.1. Materials and Methods
6.1.1. Mice

Efficacy of the treatment regimens was assessed in mice BALB/cJ mice (Jackson Laboratories, Bar Harbor, Me.). A wound of 16.6 mm was inflicted on the dorsal skin (full thickness). Mice were deeply anesthetized and dorsal skin was shaved. A circle of 16.6 mm was traced on the dorsal skin and an incision was made along the circumference. The circle of skin was then lifted off.

6.1.2. Gp96 Purification

Tissue (liver) was obtained from BALB/cJ mice and processed for purification of hsp-peptide complexes as described earlier (Srivastava et al., 1986, Proc. Natl. Acad. Sci. USA 83: 3407–3411). In all experiments, gp96 was prepared as a complex with endogenous peptide.

6.1.3. Administration

Gp96-peptide complexes were quantified using spectrometric analysis and appropriate protein quantities were resuspended prior to injection in 200 µl buffer (LPS-free LAL water) per dose. LPS equivalent to the appropriate protein quantities of gp96-peptide complex was suspended in 200 µl buffer. Injections of gp96-peptide complex or LPS, on days 0, 2, 5, and 7 post-operation, were administered intradermally either locally (i.e., near the wound site) or ventrally in each mouse.

6.1.4. Monitoring

Monitoring was performed on days 0, 2, 5, 7, 9, and 11 post-operation. Wound diameter was measured in two axes.

6.2. Results

Figure 1A:
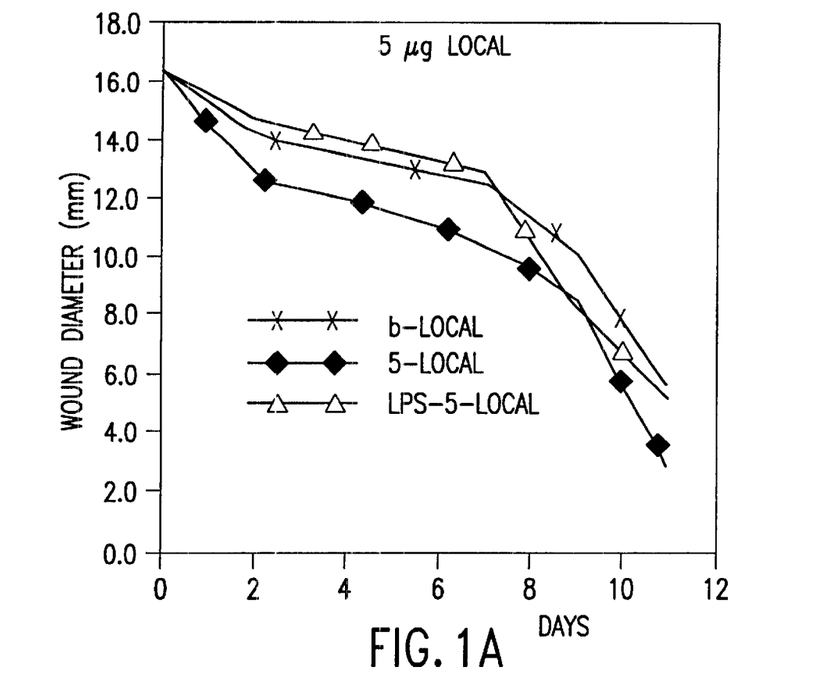
FIGS. 1A–1D. Effect of gp96-peptide complex on the rate of wound healing in BALB/cJ mice. Days post-operation are plotted on the X-axis. Wound diameter (mm) is plotted on the Y-axis. For each experiment, mice receiving treatment with buffer (lipopolysaccharide (LPS)-free water) alone served as controls. A wound having a diameter of 16.6 mm was inflicted on the dorsal skin (full thickness) of BALB/cJ mice. Mice were injected intradermally with 200 μl of buffer, liver derived gp96-peptide complex, or LPS, on days 0, 2, 5, and 7, post-operation. Wound diameter was measured (in two axes) on days 0, 2, 5, 7, 9, and 11 post-operation. Buffer was used as the diluent. Results are presented as the mean wound diameter of 4 mice/group. Key: X=Buffer alone; ○=Liver derived gp96-peptide complex; Δ=LPS.
Figure 1B:
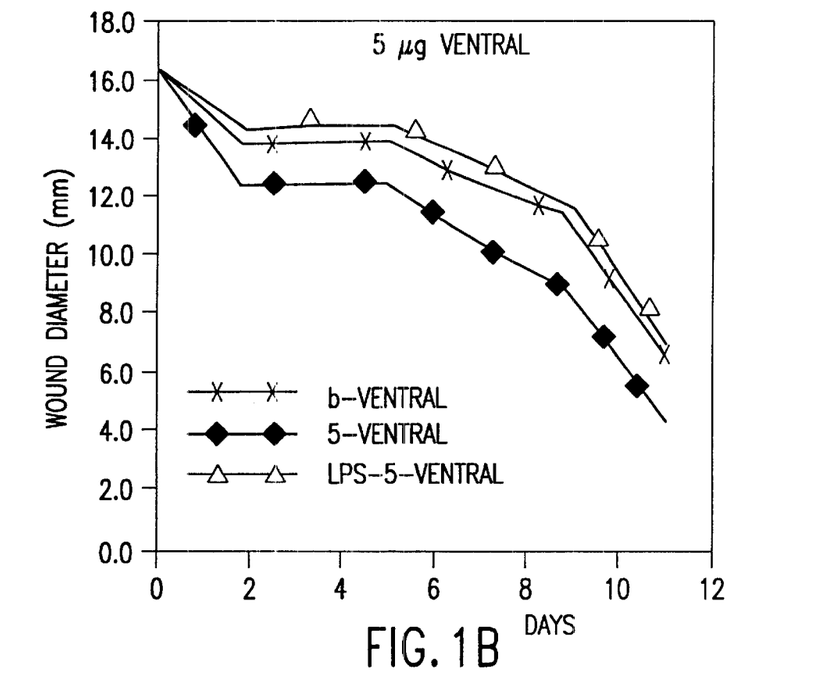
Figure 1C:
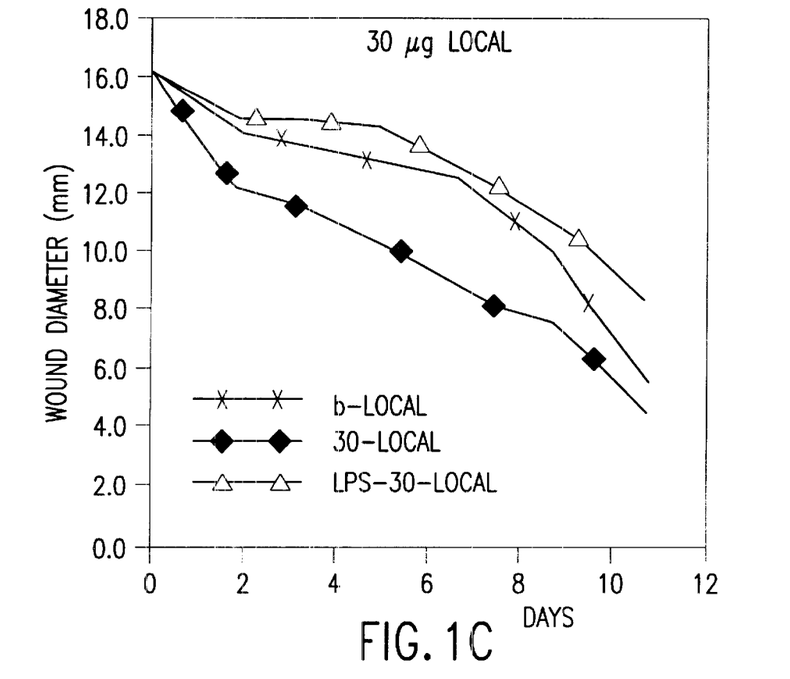
Figure 1D:
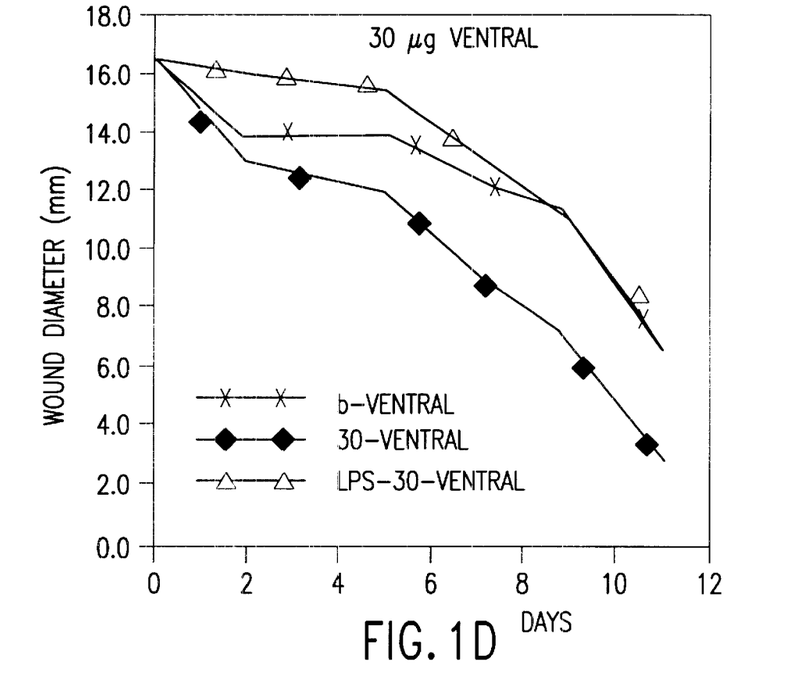
Figure 2:
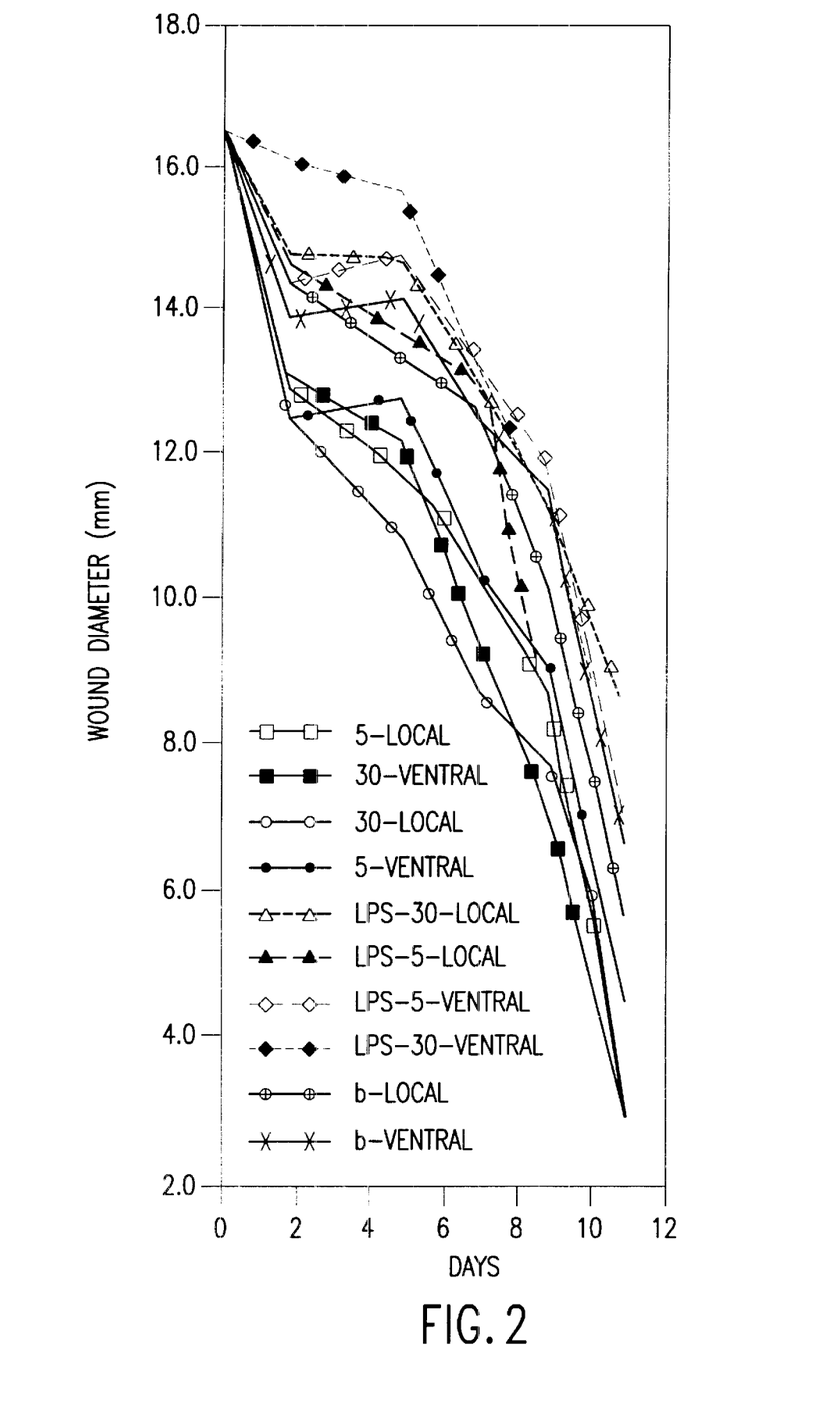

In all experiments, each gp96-peptide complex sample was obtained and used as a complex with endogenous peptide. BALB/cJ mice were administered liver-derived gp96-peptide complex or LPS in the doses specified: Liver-derived gp96-peptide complex and LPS, each in doses of 5 µg (FIGS. 1A and 1B), and 30 µg (FIGS. 1C and 1D) for each group of four animals. Administration schedules were as described in Section 6.1.3, above. Control animals were administered buffer. Administrations were injected intradermally, either locally (FIGS. 1A and 1C) or ventrally (FIGS. 1B and 1D). As shown in FIGS. 1A–1D and FIG. 2, gp96-peptide complex accelerated wound healing. In contrast, LPS adversely affected wound healing. There was a dose-related response, wherein, the higher dose (30 µg) had a greater therapeutic effect.

These results demonstrate that administration of gp96-peptide complex in accordance with the invention is useful for acceleration of wound healing.

7. EXAMPLE

Administration of Meth A Derived GP-96 Peptide Complex Accelerates Wound Healing These results indicate that administration of hsps, regardless of the source of the hsps, in accordance with the methods described below is an effective therapeutic modality for the promotion of tissue repair.

7.1. Materials and Methods
7.1.1. Mice

Efficacy of the treatment regimens was assessed in mice BALB/cJ mice (Jackson Laboratories, Bar Harbor, Maine). A wound of 27 mm was inflicted on the dorsal skin (full thickness) as described in Section 6.1, supra.

7.1.2. Gp96 Purification

Gp96-peptide complexes were obtained from meth-A induced tumors in BALB/cJ mice and processed for purification of hsp-peptide complexes as described earlier (Srivastava et al., 1986, Proc. Natl. Acad. Sci. USA 83: 3407–3411). In all experiments, gp96 was prepared as a complex with endogenous peptide.

7.1.3. Administration

Meth A derived gp96-peptide complexes were quantified using spectrometric analysis and appropriate protein quantities were resuspended prior to injection in 200 µl buffer per dose. Injections of meth A derived gp96-peptide complex, on days 0, 1, 3, 8, and 11 post-operation, were administered intradermally or subcutaneously either locally (i.e., near the wound site) or ventrally in each mouse in a dose of 1 µg or 5 µg.

7.1.4. Monitoring

Monitoring was performed on days 0, 1, 3, 8, 11, 14, and 17 post-operation. Wound diameter was measured in two axes.

7.2. Results

Figure 3A:
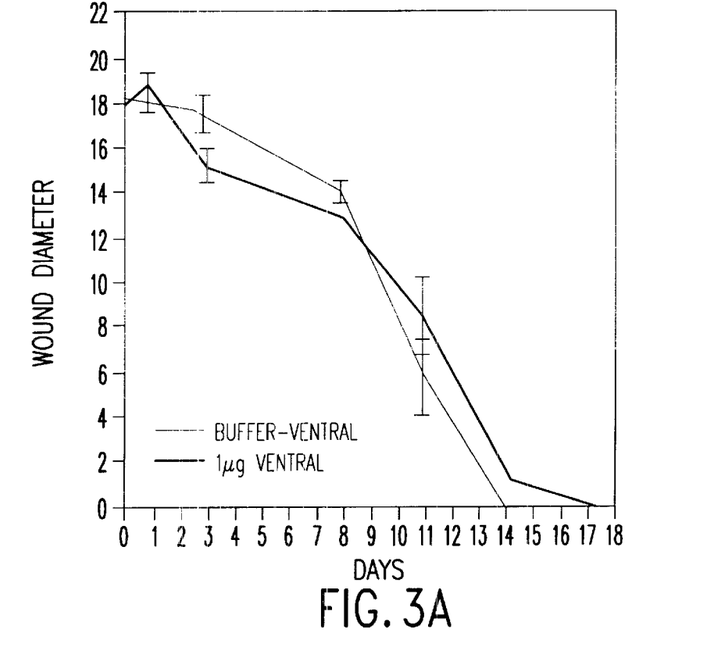
Figure 3B:
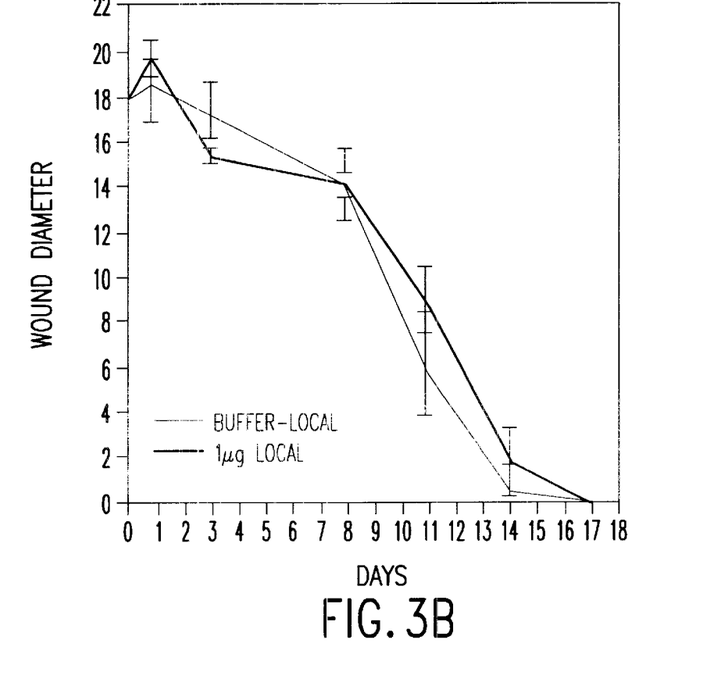
Figure 3C:
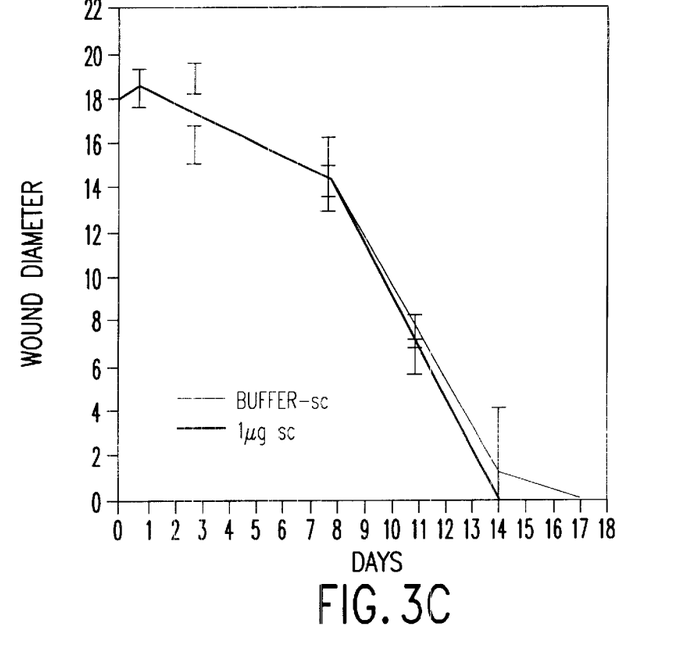
Figure 3D:
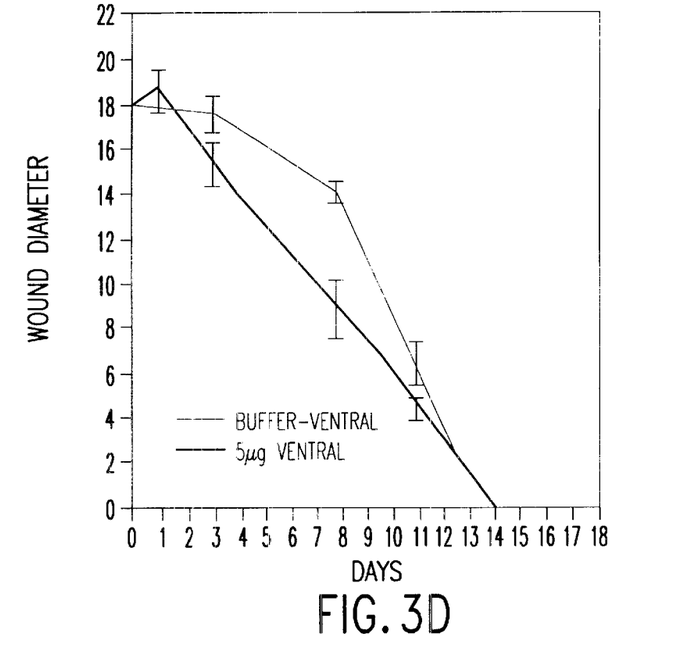
Figure 3E:
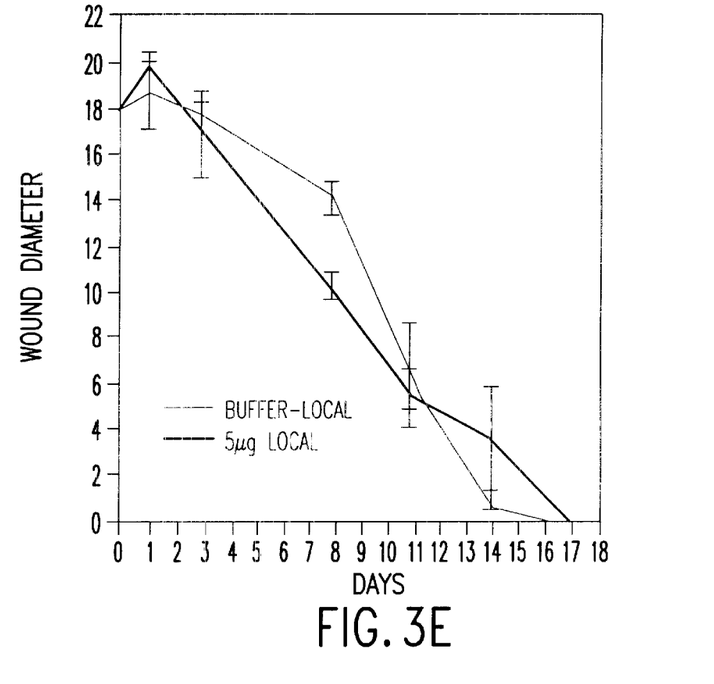
Figure 3F:
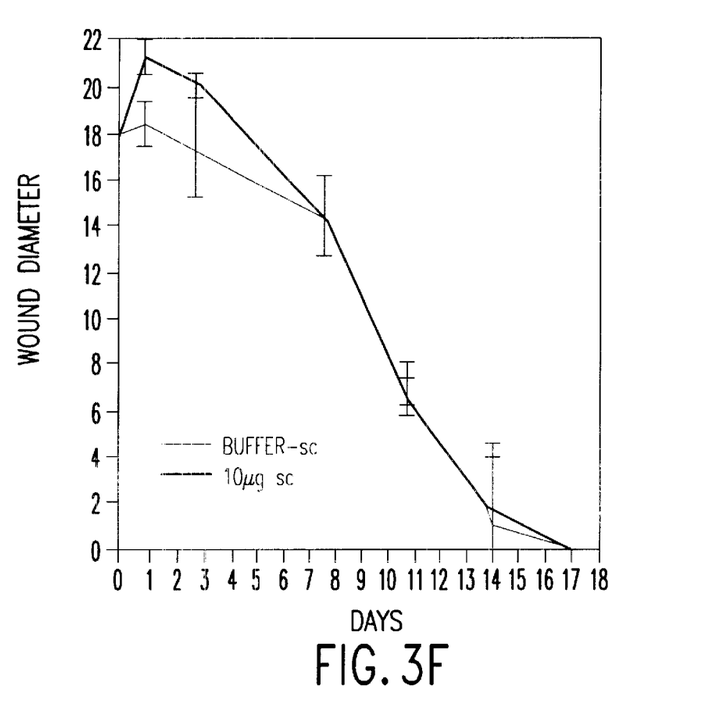

In all experiments, each gp96-peptide complex sample was obtained and used as a complex with endogenous peptide. BALB/cJ mice were administered meth A-derived gp96-peptide complex or LPS in the doses specified: meth A-derived gp96-peptide complex in doses of 1 μg (FIGS. 3A–3C), and 5 μg (FIGS. 3D–3F) for each group of five animals. Administration schedules were as described in Section 7.1.3, above. Control animals were administered buffer. Administrations were injected either intradermally, ventrally (FIGS. 3A and 3D) or locally (FIGS. 3B and 3E) or subcutaneously (FIGS. 3C and 3F). As shown in FIGS. 3A–3F, gp96-peptide complex accelerated wound healing. In contrast, LPS adversely affected wound healing.

These results demonstrate that administration of gp96-peptide complexes (derived from normal tissue or tumor) in accordance with the invention is useful for acceleration of wound healing.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of promoting skin repair in a mammal comprising administering to a mammal in need of such treatment a composition comprising a purified complex of heat shock protein noncovalently bound to a peptide or protein in an amount effective to promote skin repair, thereby promoting skin repair.

2. A method of promoting skin repair in a mammal comprising administering to a mammal in need of such treatment a composition comprising a purified heat shock protein in an amount effective to promote skin repair, wherein the heat shock protein is an hsp70 or an hsp90 family member, thereby promoting skin repair.

3. The method of claim 2 wherein the heat shock protein is not complexed to any other molecules.

4. The method of claim 1 wherein the purified heat shock protein is a member of the hsp90 family.

5. The method of claim 3 wherein the purified heat shock protein is a member of the hsp90 family.

6. The method of claim 1, 2, 3, or 4, wherein the mammal is human.

7. The method of claim 4 or 5 wherein the heat shock protein is gp96.

8. The method of claim 4 or 5 wherein the heat shock protein is hsp90.

9. The method of claim 1 or 3 wherein the heat shock protein is hsp70.

10. The method of claim 7 wherein the amount of the heat shock protein present in the composition is in a range of 1 μg to 5000 μg.

11. The method of claim 7 wherein the amount of the heat shock protein present in the composition is in a range of 5 μg to 1500 μg.

12. The method of claim 7 wherein the amount of the heat shock protein present in the composition is in a range of 30 μg to 500 μg.

13. The method of claim 7 wherein the amount of the heat shock protein present in the composition is in a range of 50 μg to 200 μg.

14. The method of claim 13 wherein the composition is administered intradermally.

15. The method of claim 1 wherein the heat shock protein is a member of the hsp70 family.

16. The method of claim 3 wherein the heat shock protein is a member of the hsp70 family.

17. The method of claim 15 or 16 wherein the mammal is human.

18. The method of claim 1 or 3 wherein the heat shock protein is hsp70, hsp90, or gp96, or a combination of any of the foregoing.

19. The method of claim 18 wherein the mammal is human.

20. The method of claim 1 or 3 wherein the skin is injured due to trauma.

21. The method of claim 20 wherein the trauma is due to burn, physical injury, or surgery.

22. The method according to claim 1 or 3, further comprising administering to the individual an effective amount of a biological response modifier selected from the group consisting of interferon-α, interferon-γ, interleukin-2, interleukin-4, interleukin-6, and tumor necrosis factor.

23. The method according to claim 1 or 3, further comprising administering to the individual an effective amount of a wound healing factor.

24. The method according to claim 23 wherein the wound healing factor is selected from the group consisting of interferon (IFN)-β, IFN-γ, interleukin (IL)-1, IL-2, IL-4, IL-5, IL-15, tumor necrosis factor, flt-1 ligand, arginine, connective tissue growth factor, adenosine, cyclic adenosine monophosphate, the fibroblast growth factor family, tumor growth factor-α, tumor growth factorβ (1 and 2), vascular endothelial growth factor, the epidermal growth factor family, the platelet derived growth factor family, the insulin-like growth factor family, nitric oxide, macrophage-stimulating protein, and macrophage-derived growth factor.

* * * * *